United States Patent
Akemi et al.

(10) Patent No.: US 8,394,404 B2
(45) Date of Patent: Mar. 12, 2013

(54) ADHESIVE MATERIAL AND ADHESIVE PREPARATION

(75) Inventors: Hitoshi Akemi, Ibaraki (JP); Kazuhisa Ninomiya, Ibaraki (JP); Hidetoshi Kuroda, Ibaraki (JP); Kensuke Matsuoka, Ibaraki (JP); Yuji Saeki, Ibaraki (JP); Masato Nishimura, Ibaraki (JP)

(73) Assignee: Nitto Denko Corporation, Ibaraki-shi (JP)

( * ) Notice: Subject to any disclaimer, the term of this patent is extended or adjusted under 35 U.S.C. 154(b) by 732 days.

(21) Appl. No.: 11/196,936

(22) Filed: Aug. 4, 2005

(65) Prior Publication Data

US 2006/0034901 A1  Feb. 16, 2006

(30) Foreign Application Priority Data

Aug. 12, 2004 (JP) ................. 2004-235646
Jul. 26, 2005 (JP) ................. 2005-215433

(51) Int. Cl.
 *A61L 15/16* (2006.01)
 *C08F 136/00* (2006.01)
(52) U.S. Cl. ..................... 424/448; 525/331.9
(58) Field of Classification Search .................. None
 See application file for complete search history.

(56) References Cited

U.S. PATENT DOCUMENTS

| | | | | |
|---|---|---|---|---|
| 4,031,894 A * | 6/1977 | Urquhart et al. | ............ | 424/448 |
| 4,588,580 A * | 5/1986 | Gale et al. | ............ | 424/449 |
| 4,657,982 A * | 4/1987 | Breck et al. | ............ | 525/240 |
| 4,806,341 A | 2/1989 | Chien et al. | | |
| 4,822,802 A | 4/1989 | Levy et al. | | |
| 4,880,416 A | 11/1989 | Horiuchi et al. | | |
| 5,163,616 A | 11/1992 | Bernarducci et al. | | |
| 5,175,052 A | 12/1992 | Tokuda et al. | | |
| 5,204,109 A | 4/1993 | Akemi et al. | | |
| 5,242,951 A | 9/1993 | Akemi et al. | | |
| 5,298,258 A | 3/1994 | Akemi et al. | | |
| 5,508,038 A * | 4/1996 | Wang et al. | ............ | 424/448 |
| 5,656,285 A | 8/1997 | Sablotsky et al. | | |
| 5,820,878 A * | 10/1998 | Hirano et al. | ............ | 424/449 |
| 5,866,157 A | 2/1999 | Higo et al. | | |
| 5,876,746 A * | 3/1999 | Jona et al. | ............ | 424/449 |
| 5,948,433 A * | 9/1999 | Burton et al. | ............ | 424/448 |
| 5,985,317 A | 11/1999 | Venkateshwaran et al. | | |
| 6,074,665 A | 6/2000 | Horstmann et al. | | |
| 6,139,866 A | 10/2000 | Chono et al. | | |
| 6,200,596 B1 | 3/2001 | Schwartzmiller et al. | | |
| 6,348,210 B1 | 2/2002 | Gale | | |
| 6,437,038 B1 | 8/2002 | Chen | | |
| 6,638,528 B1 | 10/2003 | Kanios | | |
| 6,669,953 B1 | 12/2003 | Kamiyama | | |
| 7,056,526 B2 | 6/2006 | Kuroda et al. | | |
| 7,718,188 B2 | 5/2010 | Ito et al. | | |
| 2003/0109819 A1* | 6/2003 | Tsuruda et al. | ............ | 602/48 |
| 2005/0042269 A1 | 2/2005 | Tateishi et al. | | |
| 2006/0013865 A1 | 1/2006 | Ito et al. | | |
| 2006/0034900 A1 | 2/2006 | Saeki et al. | | |
| 2009/0068486 A1 | 3/2009 | Blackwell et al. | | |

FOREIGN PATENT DOCUMENTS

| | | |
|---|---|---|
| CA | 2172738 A1 | 4/1995 |
| CN | 1171736 A | 1/1998 |
| EP | 0 337 358 A2 | 10/1989 |
| EP | 0 430 608 B1 | 2/1995 |
| EP | 0 788 792 A1 | 8/1997 |
| EP | 1 002 838 A1 | 5/2000 |
| EP | 0 430 608 A1 | 6/2001 |
| EP | 1 159 972 A2 | 12/2001 |
| EP | 1 238 664 A1 | 9/2002 |
| EP | 1002838 * | 5/2004 |
| JP | H01-261328 A | 10/1989 |
| JP | 01-287024 A | 11/1989 |
| JP | 03-220120 A | 9/1991 |
| JP | 03-223212 A | 10/1991 |
| JP | 05-176979 A | 7/1993 |
| JP | 05-177920 A | 7/1993 |
| JP | 08-502727 A | 3/1996 |
| JP | 09-099050 A | 4/1997 |
| JP | 10-151185 A | 6/1998 |
| JP | 10-152434 A | 6/1998 |
| JP | 2000-344697 A | 12/2000 |
| JP | 2001-29383 A | 2/2001 |
| JP | 2001-199937 A | 7/2001 |
| JP | 2003-226609 A | 8/2003 |
| RU | 2194496 C2 | 12/2002 |
| TW | 200413034 A | 8/2004 |
| WO | WO 94/04109 A1 | 3/1994 |
| WO | WO 96/016642 A1 | 6/1996 |
| WO | WO 00/42958 A1 | 7/2000 |
| WO | WO 01/43729 A1 | 6/2001 |
| WO | WO 03/037393 A1 | 5/2003 |
| WO | WO 2004/035054 A1 | 4/2004 |

OTHER PUBLICATIONS

Captured from http://www.arakawaeurope.com/pdfs/SIS052002-1.pdf with a date of May 2000 at bottom at of capture.*

(Continued)

*Primary Examiner* — Patricia A Duffy
*Assistant Examiner* — Garen Gotfredson
(74) *Attorney, Agent, or Firm* — Leydig, Voit & Mayer, Ltd.

(57) ABSTRACT

The present invention provides an adhesive material to be adhered to the skin etc., which maintains, for a certain time period after adhesion thereof to the skin surface, suitable adhesiveness that does not allow easy peeling or cause irritation to the skin, and which permits, when it is to be peeled off from the skin surface after the lapse of a desired certain time period, easy peeling without causing pain or physical irritation, and an adhesive preparation containing the adhesive material and a percutaneously absorbable drug in the adhesive layer. Specifically, the present invention provides an adhesive material containing a support and an adhesive layer laminated on one surface of the support, wherein the adhesive layer has an apparent viscosity at 30° C. of $0.2 \times 10^4$ to $10 \times 10^4$ Pa·s and comprises two kinds of synthetic rubbers having different flowability.

11 Claims, No Drawings

OTHER PUBLICATIONS

Handbook of Elastomers, p. 882, eds Bhowmick and Stephens, 2000.*
Venkatraman et al., *Biomaterials*, 19: 1119-1136 (1998).
Arakawa Kagaku Co. Ltd., *Technical Information of Arkon Series*.
BASF, "Technical Information—Oppanol® B 100, Oppanol® B 150, Oppanol® B 200," *TI/ES 1417 us*: 1-10 (Apr. 2003).
BASF, "Technical Information—Oppanol® B Types," *TI/ES 1482 us*: 1-8 (Sep. 2003).
Office Action from Japanese Patent Office in JP 2005-215433 (Jan. 5, 2011).
Iwata et al., "Deterioration of Cross-Linked Polyethylene Due to Water Treeing" in 1972 Annual Report—Conference on Electrical Insulation and Dielectric Phenomena (National Academy of Sciences, 1972), pp. 200-210.
Arakawa Europe GmbH, Arkon P-100 Product Data Sheet (May 2000).
Roy et al., *J. Pharm. Sci.*, 85: 5, 491-495 (1996).
Chinese Patent Office, Office Action in CN 2005-10089398.1 (Jun. 20, 2008).
Chinese Patent Office, Office Action in CN 2005-10089399.6 (Jul. 18, 2008).
European Patent Office, Office Action setting forth Third Party Observations in EP 05107128.0 (Feb. 12, 2009).
Japanese Patent Office, Office Action in JP 2005-215433 (Sep. 30, 2010).
Japanese Patent Office, Notice of Reasons for Refusal in Japanese Patent Application No. 215405/2005 (Feb. 15, 2011).
Russian Patent Office, Official Action in RU 2005-124859/15 (Jan. 23, 2009).
Russian Patent Office, Official Action in RU 2005-124860/15 (Jan. 23, 2009).
Taiwan Patent Office, Examination Report in Taiwan Patent Application 094126151 (Feb. 8, 2011).
European Patent Office, Extended European Search Report in EP 05107127 (Nov. 11, 2005).
European Patent Office, Extended European Search Report in EP 05107128 (Jun. 6, 2006).
Canadian Patent Office, Office Action in Canadian Patent Application No. 2,514,636 (Oct. 12, 2011).

* cited by examiner

ADHESIVE MATERIAL AND ADHESIVE PREPARATION

FIELD OF THE INVENTION

The present invention relates to an adhesive material for adhesion to the skin surface, which comprises an adhesive layer laminated on one surface of a support, which has suitable adhesiveness while it is adhered and which can be peeled off easily when it is detached, and an adhesive preparation comprising a percutaneously absorbable drug in an adhesive layer of the adhesive material.

BACKGROUND OF THE INVENTION

In recent years, various adhesion-type percutaneously absorbable preparations for continuous administration of a drug from the skin surface have been developed and become commercially available. The technical direction they pursue from now on will be toward maintenance of superior drug absorbability while suppressing skin irritation that occurs upon adhesion and peeling off of the preparation.

However, too much emphasis on the suppression of physical stimulation upon peeling off, which leads to unnecessarily reduction of the adhesive force, undesirably impairs adhesiveness of adhesive preparation. Particularly, in the case of a percutaneously absorbable adhesive preparation containing a drug, falling off of the preparation during the effective period becomes a serious defect that loses effectiveness as a pharmaceutical product.

To suppress physical irritation upon peeling off, for example, a method ensuring an adequate adhesive force and suppressing damages on the keratin layer upon peeling off of adhesive preparation by constituting a special gel structure (JP-B-2700835, JP-B-2970772), a method using a highly permeable support and a special adhesive (JP-B-2524190), a method using an adhesive layer designed to be re-adherable, wherein the adhesion site is changed during the effective period (U.S. Pat. No. 6,348,210) and the like have been disclosed. However, none has ever existed which takes note of changing the peelability between the initial stage of adhesion and at the time of peeling off, thereby to maintain fine drug absorbability and suppress skin irritation caused by adhesion and peeling off.

SUMMARY OF THE INVENTION

It is an object of the present invention to provide an adhesive material for adhesion to the skin surface, which has suitable adhesiveness that does not allow easy peeling off thereof for a certain time period after the adhesion to the skin surface, that does not cause skin irritation, and that allows easy peeling off from the skin surface without a pain or physical irritation after a certain, desired time period, and an adhesive preparation comprising a percutaneously absorbable drug in the adhesive material.

The present inventors have conducted intensive studies in an attempt to solve the above-mentioned problems and took note of changing the peelability of an adhesive material, which comprises an adhesive layer laminated on one surface of a support, between the initial stage of adhesion and at the time of peeling off. They have further investigated and found that an adhesive layer having an apparent viscosity at 30° C. of $0.2 \times 10^4$-$10 \times 10^4$ Pa·s and comprising two kinds of synthetic rubbers having different flowability can solve the above-mentioned problem, which resulted in the completion of the present invention.

Accordingly, the present invention provides the following.
(1) An adhesive material comprising a support and an adhesive layer laminated on one surface of the support, wherein the adhesive layer has an apparent viscosity at 30° C. of $0.2 \times 10^4$ to $10 \times 10^4$ Pa·s and comprises two kinds of synthetic rubbers having different flowability.
(2) The adhesive material of the above-mentioned (1), wherein the above-mentioned adhesive layer may further comprise a tackifier.
(3) The adhesive material of the above-mentioned (2), wherein the above-mentioned adhesive layer further comprises an organic liquid compatible with the above-mentioned two kinds of synthetic rubbers and the tackifier.
(4) The adhesive material of the above-mentioned (3), wherein the organic liquid is contained in a proportion of not more than 20% of the total weight of the above-mentioned adhesive layer.
(5) The adhesive material of the above-mentioned (1) or (2), wherein the two kinds of synthetic rubbers comprise a first synthetic rubber, which is a branched aliphatic hydrocarbon having a Staudinger Index of 170-300 $cm^3/g$, and a second synthetic rubber, which is a branched aliphatic hydrocarbon having a Staudinger Index of 30-60 $cm^3/g$.
(6) The adhesive material of the above-mentioned (5), wherein the branched aliphatic hydrocarbon is a 2-methylpropene polymer.
(7) The adhesive material of the above-mentioned (2), wherein the tackifier is an ethylethylene polymer, a 1,2-dimethylethylene polymer or an ethylethylene-1,2-dimethylethylene copolymer having a kinematic viscosity at 40° C. of 200-4000 $mm^2/s$.
(8) The adhesive material of the above-mentioned (2), wherein the tackifier is an alicyclic saturated hydrocarbon resin having a softening point of 70-125° C.
(9) The adhesive material of the above-mentioned (2), wherein the two kinds of synthetic rubbers comprise a first synthetic rubber and a second synthetic rubber having a lower Staudinger Index than the first synthetic rubber, and a mixing ratio of the first synthetic rubber:the second synthetic rubber: tackifier is 10:12-20:7-11 by weight.
(10) The adhesive material of the above-mentioned (2), wherein the two kinds of synthetic rubbers comprise a first synthetic rubber and a second synthetic rubber having a lower Staudinger Index than the first synthetic rubber, and a mixing ratio of the first synthetic rubber:the second synthetic rubber: tackifier is 10:12-20:2-6 by weight.
(11) The adhesive material of the above-mentioned (2), wherein the two kinds of synthetic rubbers comprise a first synthetic rubber and a second synthetic rubber having a lower Saudinger Index than the first synthetic rubber, and a mixing ratio of the first synthetic rubber:the second synthetic rubber: tackifier is 10:25-45:0-2 by weight.
(12) The adhesive material of the above-mentioned (3) or (4), wherein the organic liquid is at least one member selected from isopropyl myristate and a branched long-chain alcohol.
(13) The adhesive material of the above-mentioned (12), wherein the branched long-chain alcohol is at least one member selected from isostearyl alcohol and octyldodecanol.
(14) The adhesive material of the above-mentioned (12) or (13), wherein the organic liquid is isopropyl myristate, the organic liquid optionally further comprises a branched long-chain alcohol, and a mixing ratio of isopropyl myristate: branched long-chain alcohol is 1:0-4 by weight.
(15) An adhesive preparation comprising a percutaneously absorbable drug in the adhesive layer of the adhesive material of above-mentioned (1)-(14).

EFFECT OF THE INVENTION

The adhesive material of the present invention has suitable adhesiveness that does not allow easy peeling off thereof for a certain time period after the adhesion to the skin surface, that does not cause skin irritation, and that allows easy peeling off from the skin surface without a pain or physical irritation after a certain, desired time period. The adhesive preparation of the present invention has suitable adhesiveness that does not allow easy peeling off thereof for a certain time period after the adhesion to the skin surface, that does not cause skin irritation, can maintain fine absorbability of a percutaneously absorbable drug, which is an active ingredient, and can be easily peeled off from the skin surface without a pain or physical irritation after a certain, desired time period. Particularly, the adhesive material of the present invention can be easily peeled off after a desired period of 1 to 3 days by changing the mixing ratio of two kinds of synthetic rubbers having different flowability and tackifier to be added to the adhesive layer. Similarly, the adhesive preparation of the present invention is useful in that it can be peeled off easily after a desired period of 1 to 3 days according to the kind of the drug therein, which is an active ingredient.

In addition, an adhesive preparation obtained by adding 5% isosorbide dinitrate (ISDN) to the adhesive material of the present invention (Example 3 below) was subjected to an in vitro permeability test using a skin removed from a mouse, and the percutaneous absorbability of ISDN was confirmed. Thus, the adhesive preparation of the present invention is useful as a percutaneously absorbable adhesive preparation for continuous administration of a drug into the body.

BEST MODE FOR CARRYING OUT THE INVENTION

The adhesive material of the present invention is characterized in that an adhesive layer is laminated on one surface of a support, and the adhesive layer contains two kinds of synthetic rubbers having different flowability and has an apparent viscosity at 30° C. of $0.2 \times 10^4$-$10 \times 10^4$ Pa·s.

Due to the above-mentioned constitution, the adhesive material has sufficient adhesiveness that does not allow easy peeling off at least in the initial stage of adhesion, maintains suitable adhesiveness, and permits peeling off with a force free of a pain or physical irritation after use.

While the support of the present invention is not particularly limited, those substantially impermeable to drug and the like, namely, those free of a decrease in the content due to the loss of a percutaneously absorbable drug, additives and the like from the adhesive layer through a support are preferable. As the support, for example, single films of polyester, nylon, saran (registered trademark), polyethylene, polypropylene, polyvinyl chloride, ethylene-ethyl acrylate copolymer, polytetrafluoroethylene, Surlyn (registered trademark), metal foil and the like, lamination films of these and the like can be used. Of these, the support is preferably a lamination film of a non-porous plastic film made from the above-mentioned material and a porous film, so as to improve the adhesive force (anchor property) between the support and an adhesive layer. In this case, the adhesive layer is preferably formed on the porous film side.

As such porous film, one capable of improving the anchor property with the adhesive layer can be employed. Specifically, paper, woven fabric, non-woven fabric, knitted fabric, mechanically perforated sheet and the like can be mentioned. Of these, from the aspects of handling property and the like, paper, woven fabric and non-woven fabric are particularly preferable. A porous film having a thickness of 10-200 µm is employed from the aspects of improved anchor property, flexibility of adhesive material and adhesive preparation as a whole, and adhesion operability and the like. In the case of a thin preparation such as a plaster type preparation and a pressure-sensitive adhesive tape type preparation, one having a thickness of 10-100 µm is employed.

When a woven fabric or a non-woven fabric is used as the porous film, the fabric weight is preferably set to 5-30 $g/m^2$, more preferably 6-15 $g/m^2$. In the present invention, the most preferable support is a lamination film of a polyester film (preferably polyethylene terephthalate film) having a thickness of 1.5-6 µm and a non-woven polyester (preferably polyethylene terephthalate) fabric having a fabric weight of 6-12 $g/m^2$.

The adhesive layer in the present invention comprises two kinds of synthetic rubbers having different flowability.

In the present invention, "having different flowability" means difference in viscoelasticity due to different molecular weights and crosslinking densities, and the difference appears in, for example, glass transition temperature and kinematic viscosity. In general, the flowability can be expressed by a Staudinger-Index and the like.

In the present invention, the Staudinger-Index is measured according to ASTM D445, ISO3104.

In the present specification, one of the two kinds of synthetic rubbers having different flowability is also referred to as the first synthetic rubber, and the other synthetic rubber having a lower Staudinger-Index value than that of the first synthetic rubber is also referred to as the second synthetic rubber.

The apparent viscosity at 30° C. of the adhesive layer in the present invention is $0.2 \times 10^4$ to $10 \times 10^4$ Pa·s, preferably $0.5 \times 10^4$ to $9.5 \times 10^4$ Pa·s. When the apparent viscosity at 30° C. is less than $0.2 \times 10^4$ Pa·s, cohesive failure markedly occurs irrespective of the duration of adhesion, and when it exceeds $10 \times 10^4$ Pa·s, the adhesive force becomes insufficient and adhesiveness becomes poor.

The apparent viscosity in the present invention is obtained by measurement the following conditions according to JIS K7210 and using a flow tester CFT-500C (manufactured by Shimadzu Corporation), and calculation by the following calculation formulas.

[Measurement Conditions]
Cylinder pressure: 30.0 $kgf/cm^2$
Die used: L: 10.00 mm, D: 1.00 mm
Preheating time: 300 s
Apparent shear stress: $7.36 \times 10^5$ $dyn/cm^2$
Measurement start position $S_1$: 3 mm
Measurement end position $S_2$: 7 mm $$Q = A \cdot \frac{S_2 - S_1}{10 \cdot \Delta t} \ (cm^3/s)$$

$$\gamma = \frac{32Q}{\pi D^3} \cdot 10^3 \ (s^{-1})$$

$$\tau = \frac{PD}{4L} \ (Pa)$$

$$\eta = \frac{\tau}{\gamma} \cdot \frac{\pi D^4 P}{128 LQ} \times 10^{-3} \ (Pa \cdot s)$$

wherein each symbol shows the following:
Q: flow rate
γ: apparent shear velocity
τ: apparent shear stress
η: apparent viscosity A: piston cross-section area (cm$^2$)
S$_1$: measurement start position (mm)
S$_2$: measurement end position (mm)
Δt: lapse of time for a piston to reach measurement end position from the measurement start position
D: die bore diameter (mm)
P: test pressure (Pa)
L: die length (mm)

As the synthetic rubber to be used in the present invention, for example, polydimethyl siloxane resin, butyl rubber, ethylene-vinylacetate copolymer, ethylene-ethylacrylate copolymer, polyalkylvinylether (e.g., polypropylvinylether, polyisopropylvinylether, polybutylvinylether etc.), 2-methylpropene polymer, ethylethylene polymer, 1,2-dimethylethylene polymer, ethylethylene-1,2-dimethylethylene copolymer, polyisoprene, polybutadiene and the like can be mentioned, with preference given to 2-methylpropene polymer, ethylethylene polymer, 1,2-dimethylethylene polymer, and ethylethylene-1,2-dimethylethylene copolymer, from the aspects of cost, handleability and the like.

As the synthetic rubber to be used in the present invention, a branched aliphatic hydrocarbon is particularly preferable. As the branched aliphatic hydrocarbon, for example, polymers and copolymers obtained from monomers such as 2-methylpropene, ethylethylene, 1,2-dimethylethylene and the like can be mentioned. Specifically, 2-methylpropene polymer, ethylethylene polymer, 1,2-dimethylethylene polymer, ethylethylene-1,2-dimethylethylene copolymer and the like can be mentioned.

In the present invention, two kinds of synthetic rubbers having different flowability are not particularly limited, but the first synthetic rubber is preferably a branched aliphatic hydrocarbon having a Staudinger-Index of 170-300 cm$^3$/g, preferably 180-290 cm$^3$/g, and the second synthetic rubber is preferably a branched aliphatic hydrocarbon having a Staudinger-Index of 30-60 cm$^3$/g, preferably 35-55 cm$^3$/g. In this case, when the Staudinger-Index of the first synthetic rubber is less than 170 cm$^3$/g, the cohesion tends to become insufficient and when it exceeds 300 cm$^3$/g, the tack of an adhesive tends to become low. When the Staudinger-Index of the second synthetic rubber is less than 30 cm$^3$/g, the adhesive shows greater stickiness, which sometimes exerts an adverse influence on peeling in a desired number of days, and when it exceeds 60 cm$^3$/g, the apparent viscosity of an adhesive becomes higher than the predetermined range, which may in turn result in a failure to adhere for the desired number of days.

As the branched aliphatic hydrocarbon when the first synthetic rubber is "a branched aliphatic hydrocarbon having a Staudinger-Index of 170-300 cm$^3$/g (preferably 180-290 cm$^3$/g)", 2-methylpropene polymer is preferable.

As the branched aliphatic hydrocarbon when the second synthetic rubber is "a branched aliphatic hydrocarbon having a Staudinger-Index of 30-60 cm$^3$/g (preferably 35-55 cm$^3$/g)", 2-methylpropene polymer, ethylethylene polymer, 1,2-dimethylethylene polymer and ethylethylene-1,2-dimethylethylene copolymer are preferable.

The proportion of the two kinds of synthetic rubbers having different flowability relative to the total weight of the adhesive layer is preferably 50-100%, more preferably 60-100%, in the total weight. The proportion of the first synthetic rubber of the two kinds of synthetic rubbers having different flowability relative to the whole weight of the adhesive layer is preferably 10-45%, more preferably 15-40%. The proportion of the second synthetic rubber having a lower Staudinger-Index value than that of the first synthetic rubber, relative to the whole weight of the adhesive layer is preferably 30-85%, more preferably 35-80%. When the adhesive layer contains a drug, the above-mentioned proportion does not include the amount of the drug.

The adhesive layer in the present invention may further contain a tackifier. By the addition of a tackifier, the adhesion period from the start of the adhesion to the skin surface until the layer comes to have peelability permitting easy peeling off can be extended. In addition, by setting the mixing ratio of the two kinds of synthetic rubbers having different flowability and a tackifier to the one exemplified below, an adhesive preparation for a desired period of adhesion suitable for the kind of the drug can be prepared.

The tackifier to be used for the present invention may be appropriately selected from those known in the field of adhesive preparations. As the tackifier, for example, polybutenes, rosin resin, terpene resin, petroleum resin, chroman resin and the like can be mentioned. From the aspect of compatibility, (i) ethylethylene polymer, 1,2-dimethylethylene polymer and ethylethylene-1,2-dimethylethylene copolymer, each having a kinematic viscosity at 40° C. of 200-4000 mm$^2$/s, preferably 500-700 mm$^2$/s; and (ii) an alicyclic saturated hydrocarbon resin having a softening point of 70-125° C., preferably 90-115° C., are preferable. When the kinematic viscosity of the above-mentioned (i) is less than 200 mm$^2$/s, the skin surface may become sticky after peeling off or the adhesive may bleed, and when it exceeds 4000 mm$^2$/s, a desired tack may not be obtained.

When the softening point of the above-mentioned (ii) is less than 70° C., the skin surface may become sticky after peeling off, the adhesive may bleed, or thermal stability may be degraded, and when it exceeds 125° C., compatibility may be degraded.

As the alicyclic saturated hydrocarbon resin having a softening point of 70-125° C., preferably 90-115° C., for example, a thermoplastic hydrogenation resin having an alicyclic structure formed by adding hydrogen to hydrocarbon resin obtained by polymerization of aromatic hydrocarbon (C9-C12) containing styrene, α-methylstyrene, vinyltoluene, indene, methylindene and the like, and the like can be mentioned.

The tackifier may be used in a combination of one or more kinds thereof.

The kinematic viscosity in the present invention is measured according to JIS K2283 and ISO3104.

The softening point in the present invention is measured according to pharmaceutical product additive standard (109992).

The proportion of the tackifier relative to the total weight of the adhesive layer is preferably 0-40%, more preferably 0-30%, in the total weight. When a drug is contained, however, the above-mentioned proportion does not include the weight of the drug.

The adhesive layer in the present invention may further contain an organic liquid compatible with the above-mentioned two kinds of synthetic rubbers having different flowability, and the above-mentioned tackifier.

The organic liquid to be used in the present invention is not particularly limited as long as it is compatible with the above-mentioned two kinds of synthetic rubbers having different flowability, and the above-mentioned tackifier, and as long as it does not lose adhesive property. When an adhesive preparation containing a drug is produced, however, the organic liquid preferably dissolves the drug, and has an absorption promoting action to improve percutaneous absorbability of the contained drug. As the organic liquid, for example, higher alcohols such as oleyl alcohol, isostearyl alcohol, octyldodecanol and the like, oils and fats such as olive oil, castor oil, squalene, lanolin and the like, organic solvents such as ethyl acetate, ethyl alcohol, dimethyldecylsulfoxide, methyloctylsulfoxide, dimethylsulfoxide, dimethylformamide, dimethylacetamide, dodecylpyrrolidone, isosorbitol and the like, plasticizer liquid surfactants such as phthalate, diethyl sebacate, triethyl citriate, tributyl acetyl citrate and the like, liquid paraffin and the like hydrocarbons, ethoxylated stearyl alcohol, glycerine fatty acid ester, isopropyl myristate, isotridecyl myristate, ethyl laurate, N-methylpyrrolidone, ethyl oleate, oleic acid, diisopropyl adipate, isopropyl palmitate, 1,3-butanediol and the like can be mentioned. These organic liquids may be used in combination of one or more kinds thereof.

Of these organic liquids, preferred are fatty acid ester and glycerine fatty acid ester (particularly fatty acid monoglyceride). While these fatty acid esters and glycerine fatty acid esters are preferable as long as they plasticize an adhesive, a fatty acid having an unnecessarily large or small number of carbons may degrade compatibility with the aforementioned synthetic rubber and the like, or may be volatilized in a heating step for producing a preparation. In addition, an organic liquid made of a fatty acid having a double bond in a molecule may give rise to a problem in the preservation stability due to oxidative degradation and the like. Moreover, when an adhesive preparation is produced, a high content of a percutaneously absorbable drug per unit area leads to the precipitation of the drug above the saturation solubility in the preparation. Depending on the kind of fatty acid ester and glycerine fatty acid ester to be added, the crystal precipitation of the drug may be inhibited or precipitation may be delayed, which in turn may degrade the appearance of the obtained preparation or may adversely affect the preservation stability.

As the fatty acid ester to be used, therefore, a fatty acid ester comprising a higher fatty acid preferably having 12 to 16, more preferably 12-14, carbon atoms and a lower monovalent alcohol having 1 to 4 carbon atoms is employed. As such higher fatty acid, preferred are lauric acid (C12), myristic acid (C14) and palmitic acid (C16), and myristic acid is particularly preferable. As the lower monovalent alcohol, methyl alcohol, ethyl alcohol, propyl alcohol and butyl alcohol can be mentioned, which may be a straight chain alcohol or a branched alcohol. Desirably, isopropyl alcohol is used. Therefore, most preferable fatty acid ester is isopropyl myristate.

As the glycerine fatty acid ester, glyceride with higher fatty acid having 8 to 10 carbon atoms is preferable. As such higher fatty acid, preferred are caprylic acid (octanoic acid, C8), pelargonic acid (nonanoic acid, C9) and capric acid (decanoic acid, C10), and particularly preferred are caprylic monoglyceride, caprylic diglyceride, caprylic triglyceride and caprilyc capric triglyceride using caprylic acid.

When a higher alcohol is used as an organic liquid, for example, a saturated or unsaturated branched long-chain alcohol having 16 to 22, preferably 18-20, carbon atoms, such as isostearyl alcohol, octyldodecanol and the like are more preferable.

An embodiment wherein the organic liquid is isopropyl myristate and a branched long-chain alcohol is optionally contained as an organic liquid is particularly preferable. In this case, the mixing ratio of isopropyl myristate and a branched long-chain alcohol is preferably 1:0-4, more preferably 1:0-3, by weight.

When the mixing ratio of the branched long-chain alcohol relative to isopropyl myristate exceeds 4 by weight, the adhesiveness during perspiration may become lower and the preparation may come off during application.

The proportion of the organic liquid relative to the total weight of the adhesive layer is preferably not more than 20% in the total weight, so as to maintain special adhesive property of the present invention.

The adhesive layer may contain, as optional components, other additives (e.g., polymers such as polyvinylpyrrolidone, aminoalkyl methacrylate copolymer, methacrylic acid copolymer and the like, esters such as sorbitan fatty acid ester, propyleneglycol fatty acid ester and the like, inorganic compounds such as magnesium aluminum silicate and the like, other inorganic or organic fillers etc.), as long as the effect of the present invention is not inhibited. The proportion of other additives as optional components is preferably not more than 15% of the total weight of the adhesive layer.

In the present invention, by setting a particular mixing ratio of two kinds of synthetic rubbers having different flowability and a tackifier, an adhesive material permitting easy peeling off in a desired period of 1 to 3 days can be prepared. Particularly, the adhesive preparation of the present invention is useful because it can be easily peeled off in a desired period of 1 to 3 days according to the kind of the drug, which is an active ingredient.

For 3 day adhesion, the mixing ratio of a first synthetic rubber of two kinds of synthetic rubbers having different flowability, a second synthetic rubber having a lower Staudinger-Index value than that of the first synthetic rubber and a tackifier is set to, for example, 10:12-20:7-11, by weight.

For 2 day adhesion, the mixing ratio of a first synthetic rubber of two kinds of synthetic rubbers having different flowability, a second synthetic rubber having a lower Staudinger-Index value than that of the first synthetic rubber and a tackifier is set to, for example, 10:12-20:2-6, by weight.

For 1 day adhesion, the mixing ratio of a first synthetic rubber of two kinds of synthetic rubbers having different flowability, a second synthetic rubber having a lower Staudinger-Index value than that of the first synthetic rubber and a tackifier is set to, for example, 10:25-45:0-2, by weight.

The thickness of the adhesive layer is generally 60 µm-200 µm, preferably 80 µm-180 µm, more preferably 100 µm-160 µm. When the thickness is less than 60 µm, sufficient adhesive force may be difficult to be secured during the adhesion period, and a thickness exceeding 200 µm is unpreferable for appropriate production and the like.

The adhesive material and adhesive preparation of the present invention can be produced by, for example, dissolving two kinds of synthetic rubbers having different flowability, a tackifier, an organic liquid, other additive as an optional component and a desired percutaneously absorbable drug in a suitable solvent such as toluene etc., applying the obtained adhesive solution to a liner (e.g., polyethylene terephthalate film subjected to a peel treatment with silicone etc.), drying the liner to form an adhesive layer, and laminating a support on the adhesive layer. Alternatively, they can be produced by, for example, directly applying the above-mentioned adhesive solution to a support and drying the support to form an adhesive layer.

A drug to be the active ingredient that can be contained in the adhesive preparation of the present invention is not particularly limited, and can be selected freely according to the treatment object. For example, percutaneously absorbable drugs of various kinds such as corticosteroids, analgesic/antiphlogistic, sedative hypnotic, tranquilizer, antihypertensive agent, hypotensive diuretic, antibiotic, anaesthetic, antibacterial agent, antifungal agent, vitamin, coronary vasodilator, antihistaminic agent, antitussive, sex hormone agent, antidepressant, cerebral circulation improver, antiemetic, antitumor agent, living organism pharmaceutical agent and the like, which do not dwell on the skin surface but penetrate subcutaneously or into the blood to exert a local effect or a systemic effect can be used. These drugs may be used in combination of two or more kinds thereof as necessary. From the aspects of uniform dispersion in the above-mentioned adhesive layer and percutaneous absorbability, liposoluble drugs (dissolved amount 0.4 g or below/water 100 ml, ambient temperature) from among these drugs are particularly preferable. It is needless to say that not only percutaneously absorbable drugs but drugs that directly act on the skin wound etc. can be contained.

While the content of these percutaneously absorbable drugs can be appropriately determined according to the kind of drug and administration object, it is generally within the range of about 1-40 wt %, preferably 3-30 wt %, in an adhesive. When the content is less than 1 wt %, release of an amount effective for the treatment or prophylaxis sometimes cannot be expected, and a content exceeding 40 wt % is economically disadvantageous because the increased amount does not lead to an increased effect and the adhesion to the skin surface may become inferior. In the present invention, the above-mentioned drugs do not need to be completely dissolved in an adhesive. They may be contained in an amount exceeding the solubility in the adhesive to contain undissolved drug as well. In this case, however, the undissolved drug needs to be uniformly dispersed in a percutaneously absorbable adhesive preparation to prevent inconsistent content of the drug.

It is needless to say that a drug may be contained in an amount exceeding the above-mentioned range of drug content for the purpose of affording long-term sustained releaseability, increasing the amount of release by increasing the content per unit area, miniaturizing the preparation in an attempt to reduce skin irritation and the like.

The form of the adhesive material and adhesive preparation of the present invention is not particularly limited and, for example, a tape, a sheet and the like are mentioned.

While the size of the adhesive material and adhesive preparation of the present invention is not particularly limited, and varies depending on the adhesion site, the kind of drug to be contained, and age, body weight, condition etc. of patient, it is generally about 10-100 $cm^2$.

It is preferable to seal the adhesive material and adhesive preparation of the present invention until before use for preservation, transportation and the like. The packaging method includes, for example, superimposing one sheet or several sheets of the adhesive material and the adhesive preparation, packing them with a packaging material, and heat-sealing the part surrounding them. The packaging material is not particularly limited and may be, for example, a sheet or a film. From the aspects of easy packaging and air tightness, heat-sealable ones are preferable. Specific examples of suitable packaging materials include those using a plastic sheet having heat sealability, such as polyethylene, Surlyn (registered trademark), ethylene-vinyl acetate copolymer, ethylene-vinyl alcohol copolymer, polyacrylonitrile copolymer, polyvinyl alcohol copolymer and the like. Particularly, a laminate of a gas impermeable film such as polyester film, metal foil and the like is preferably used to prevent volatilization, scattering and the like of a percutaneously absorbable drug contained in the adhesive preparation. As the packaging material, one having a thickness of generally 10 μm-200 μm is used.

Particularly, for an adhesive preparation containing a drug to be the active ingredient, the above-mentioned packaging material comprising a polyacrylonitrile copolymer having high barrier property in the innermost layer is more preferable. Moreover, out of the fear of degradation of handling property (e.g., easy taking out from a package) caused by the bleeding of the adhesive component due to the special adhesive property of the present invention, some design may be preferably employed, which is exemplified by a peel treatment or an emboss processing of the packaging material, a dry etching processing to somewhat enlarge the below-mentioned liner part than the preparation, a package formed by blister molding to reduce the contact area and the like.

The adhesive material and adhesive preparation of the present invention preferably have a release liner laminated thereon to protect the adhesive surface of an adhesive layer until use. The release liner is not particularly limited as long as it can be subjected to a peel treatment and certainly has a sufficient peelability. Examples thereof include films of polyester, polyvinyl chloride, polyvinylidene chloride, polyethylene terephthalate and the like, paper such as quality paper, glassine and the like, a laminate film of quality paper, glassine etc. with polyolefin, and the like, which have been subjected to a peel treatment comprising applying silicone resin, fluororesin and the like to the surface to be in contact with the adhesive layer. The thickness of the release liner is generally 10-200 μm, preferably 25-100 μm.

The release liner to be used for the adhesive preparation containing a drug is preferably made from a polyester (preferably, polyethylene terephthalate) resin, from the aspects of barrier property and cost. Moreover, the thickness is more preferably about 25-100 μm.

The adhesive material and adhesive preparation of the present invention can be used by taking out by tearing the above-mentioned package immediately before use, removing the release liner, and adhering the exposed adhesive surface to the skin surface.

The adhesive material and adhesive preparation of the present invention can be easily peeled off from the skin surface without a pain or physical irritation after a desired period of 1 to 3 days previously determined based on the kind of drug.

In the case of adhesion for not less than 4 days, irritation etc. caused by being sealed and closed may not be dealt with, and sufficient adhesion property may not be necessarily maintained. Thus, the adhesion period in the present invention is preferably up to 3 days.

EXAMPLES

The present invention is explained in detail in the following by referring to Examples, which are not to be construed as limitative. In the following, "part" and "%" mean "parts by weight" and "wt %", respectively.

Examples 1-12, Comparative Examples 1-5

Each composition of Table 1-4 was dissolved in toluene to give a coating solution having a solute concentration of 35%. This solution was applied to a polyethylene terephthalate (PET) liner after a silicone peel treatment, such that the thickness of the coating after drying became 120 μm. This was dried in a hot-air circulation oven at 70° C. for 2 min, 80° C. for 2 min and 95° C. for 3 min to give an adhesive layer. A non-woven fabric surface of a support made of a 2 μm thick PET film and a PET non-woven fabric (12 $g/m^2$) adhered to each other with a polyester adhesive was laminated on the adhesive layer. This laminate was aged at room temperature for 2 days to give adhesive sheets of Examples 1-12 and Comparative Examples 1-5 of the present invention.

For measurement of the apparent viscosity, a sample free of lamination of the above-mentioned support, and having only an adhesive layer was recovered.

In the following Tables 1-4, each symbol means the following.

A: first synthetic rubber 2-methylpropene polymer

B: second synthetic rubber 2-methylpropene polymer

T1: tackifier 1,2-dimethylethylene polymer having a kinematic viscosity at 40° C. of 600 mm$^2$/s T2: tackifier alicyclic saturated hydrocarbon resin having a softening point of 100° C.

$J_0$: Staudinger-Index

IPM: isopropyl myristate

ISO: isostearyl alcohol

TABLE 1

Composition of 3 day adhesive material.

| | A | | B | | tackifier | | additive | |
| | | | | | T1 | T2 | IPM | ISO |
| Ex. No. | $J_0$ | Mixing ratio | $J_0$ | Mixing ratio | mixing ratio | mixing ratio | addition (%) | addition (%) |
|---|---|---|---|---|---|---|---|---|
| 1 | 274 | 10 | 35 | 20 | 7 | — | 5 | — |
| 2 | 274 | 10 | 35 | 12 | 7 | — | 10 | 5 |
| 3 | 211 | 10 | 35 | 15 | 9 | — | 5 | 5 |
| 4 | 211 | 10 | 35 | 12 | — | 11 | 10 | — |
| 5 | 211 | 10 | 35 | 20 | — | 11 | — | — |

TABLE 2

Composition of 2 day adhesive material

| | A | | B | | Tackifier | | Additive |
| | | | | | T1 | T2 | IPM |
| Ex. No. | $J_0$ | Mixing ratio | $J_0$ | Mixing ratio | mixing ratio | mixing ratio | addition (%) |
|---|---|---|---|---|---|---|---|
| 6 | 211 | 10 | 35 | 20 | — | 2 | 10 |
| 7 | 211 | 10 | 35 | 15 | — | 4 | 10 |
| 8 | 211 | 10 | 35 | 12 | 6 | — | 10 |
| 9 | 211 | 10 | 35 | 20 | 6 | — | — |

TABLE 3

Composition of 1 day adhesive material

| | A | | B | | tackifier | | additive |
| | | | | | T1 | T2 | IPM |
| Ex. No. | $J_0$ | Mixing ratio | $J_0$ | Mixing ratio | mixing ratio | mixing ratio | addition (%) |
|---|---|---|---|---|---|---|---|
| 10 | 274 | 10 | 49 | 40 | — | — | — |
| 11 | 274 | 10 | 49 | 35 | — | — | — |
| 12 | 274 | 10 | 49 | 25 | 2 | — | 10 |

TABLE 4

Composition of Comparative Example

| | A | | B | | tackifier | | additive |
| | | | | | T1 | T2 | IPM |
| Com. Ex. No. | $J_0$ | Mixing ratio | $J_0$ | Mixing ratio | mixing ratio | mixing ratio | addition (%) |
|---|---|---|---|---|---|---|---|
| 1 | 423 | 10 | 35 | 15 | — | 9 | 15 |
| 2 | 140 | 10 | 35 | 12 | — | 7 | — |
| 3 | 211 | 10 | 35 | 10 | 5 | — | 10 |
| 4 | 211 | 10 | 35 | 50 | — | — | — |
| 5 | 274 | 10 | 35 | 30 | 15 | — | 5 |

The physical property was measured by the following method.

<Measurement of Staudinger-Index>

The Staudinger-Index $J_0$ (cm$^3$/g) was measured according to ASTM D445, ISO3104 under the following conditions.

viscosimeter: Ubbelohde Capillary 1
measurement temperature: 20° C.
sample concentration
$J_0$<150:0.01 g/cm$^3$ isooctane
150<$J_0$<400:0.002 g/cm$^3$ isooctane
400<$J_0$:0.001 g/cm$^3$ isooctane
$J_0 = \eta_{sp}/c(1+0.31\eta_{sp})$ cm$^3$/g (Schulz-Blaschke)
$\eta_{sp} = t/t_0 - 1$
t=flow time of solution (Hagenbach-couette correction)
$t_0$=flow time of solvent (Hagenbach-couette correction)
c=concentration of solution <Measurement of Kinematic Viscosity>

Measured according to JIS K2283 and ISO3104.

<Measurement of Softening Point>

Measured according to pharmaceutical product additive standard (109992).

Experimental Example 1

Measurement of Apparent Viscosity Measurement of Adhesive Force

The adhesive materials of Examples 1-12 and Comparative Examples 1-5 were measured for apparent viscosity and adhesive force according to the following methods. The results are shown in Table 5.

<Measurement of Apparent Viscosity>

The aforementioned samples were subjected to the measurement under the following conditions using a flow tester CFT-500C (manufactured by Shimadzu Corporation) according to JIS K7210 and the values were used for the calculation by the following formulas. The sample density used was 1.0 g/cm$^2$.

[Measurement Conditions]
sample temperature: 30° C.
cylinder pressure: 30.0 kgf/cm$^2$
die used: L: 10.00 mm, D: 1.00 mm
preheating time: 300 s
apparent shear stress: 7.36×10$^5$ dyn/cm$^2$
Measurement start position $S_1$: 3 mm
Measurement end position $S_2$: 7 mm

[Calculation Equations]

$$Q = A \cdot \frac{S_2 - S_1}{10 \cdot \Delta t} \text{ (cm}^3\text{/s)}$$

-continued $$\gamma = \frac{32Q}{\pi D^3} \cdot 10^3 \; (s^{-1})$$

$$\tau = \frac{PD}{4L} \; (Pa)$$

$$\eta = \frac{\tau}{\gamma} \cdot \frac{\pi D^4 P}{128 LQ} \times 10^{-3} \; (Pa \cdot s)$$

Each symbol in the equations shows the following.
Q: flow rate
γ: apparent shear velocity
τ: apparent shear stress
η: apparent viscosity
A: piston cross-section area (cm$^2$)
$S_1$: measurement start position (mm)
$S_2$: measurement end position (mm)
Δt: lapse of time for a piston to reach measurement end position from the measurement start position
D: die bore diameter (mm)
P: test pressure (Pa)
L: die length (mm)

<Measurement of Adhesive Force>

A belt-like sample cut out in width 12 mm, length 200 mm was adhered to a bakelite plate, allowed to closely adhere by one reciprocation of a roller (load 850 g), left standing at 23° C. for 20 min, peeled off in a 180° direction at 300 mm/min under 23° C., 60% RH conditions with a tension tester, and the peelability then was measured.

TABLE 5

Adhesive force and apparent viscosity

| Sample | Adhesive force (N/12 mm) | Apparent viscosity (Pa · s) |
|---|---|---|
| Example 1 | 5.8 | 1.04 × 10$^4$ |
| Example 2 | 7.5 | 0.59 × 10$^4$ |
| Example 3 | 6.3 | 1.58 × 10$^4$ |
| Example 4 | 6.5 | 1.32 × 10$^4$ |
| Example 5 | 5.3 | 1.40 × 10$^4$ |
| Example 6 | 5.5 | 2.41 × 10$^4$ |
| Example 7 | 4.9 | 3.10 × 10$^4$ |
| Example 8 | 6.2 | 5.04 × 10$^4$ |
| Example 9 | 4.8 | 5.72 × 10$^4$ |
| Example 10 | 4.4 | 8.51 × 10$^4$ |
| Example 11 | 4.0 | 9.21 × 10$^4$ |
| Example 12 | 5.5 | 6.65 × 10$^4$ |
| Com. Example 1 | 2.6 | 17.4 × 10$^4$ |
| Com. Example 2 | 10.4 | 0.14 × 10$^4$ |
| Com. Example 3 | 4.5 | 12.6 × 10$^4$ |
| Com. Example 4 | 5.4 | 0.08 × 10$^4$ |
| Com. Example 5 | 7.1 | 0.18 × 10$^4$ |

Experimental Example 2

Human Adhesion Test

The adhesive materials of Examples 1-12 and Comparative Examples 1-5 were prepared in length 10 cm and adhered to the inner side of the antebrachial region of volunteers (n=3). The peelability was measured at 2 hr after adhesion, 1 day after adhesion, 2 days after adhesion and 3 days after adhesion under the same conditions as in the adhesive force measurement in the aforementioned Experimental Example 1. The direction of peeling off was the 90° direction. In addition, the presence of pain upon peeling off was also confirmed. The result of the peelability was an average value and the result of the presence of pain followed the opinion of the majority. The results are shown in Table 6.

In Table 6, in the column of pain upon peeling off, ○ means "no pain", Δ means "a little pain", × means "considerable pain", "note 1" means "non-peelable due to cohesive failure", "note 2" means "not measureable due to falling off of the sample from the adhesion site", "note 3" means "not measured due to destruction (relocation) of sample by severe cohesive failure".

TABLE 6

Adhesion test

| Sample | 2 hr later Peelability (N/12 mm) | 2 hr later Pain upon peeling | 1 day later Peelability (N/12 mm) | 1 day later Pain upon peeling | 2 days later Peelability (N/12 mm) | 2 days later Pain upon peeling | 3 days later Peelability (N/12 mm) | 3 days later Pain upon peeling |
|---|---|---|---|---|---|---|---|---|
| Ex. 1 | 14.8 | × note 1 | 5.18 | Δ | 2.36 | ○ | 1.18 | ○ |
| Ex. 2 | 15.2 | × note 1 | 3.95 | Δ | 1.98 | ○ | 1.35 | ○ |
| Ex. 3 | 13.6 | × note 1 | 4.44 | Δ | 2.51 | ○ | 1.25 | ○ |
| Ex. 4 | 12.9 | × note 1 | 3.02 | Δ | 2.27 | ○ | 1.10 | ○ |
| Ex. 5 | 14.0 | × note 1 | 3.21 | Δ | 1.75 | ○ | 1.69 | ○ |
| Ex. 6 | 14.8 | × note 1 | 2.92 | Δ | 1.66 | ○ | | |
| Ex. 7 | 13.1 | × note 1 | 3.11 | Δ | 1.95 | ○ | | |
| Ex. 8 | 12.6 | × note 1 | 5.01 | Δ | 1.35 | ○ | | |
| Ex. 9 | 12.9 | × note 1 | 3.44 | Δ | 2.26 | ○ | | |
| Ex. 10 | 11.1 | × note 1 | 1.63 | ○ | | | | |
| Ex. 11 | 12.6 | × note 1 | 1.51 | ○ | | | | |
| Ex. 12 | 12.9 | × note 1 | 1.70 | ○ | | | | |
| Com. Ex. 1 | 3.48 | Δ | — | — | note 2 | | | |
| Com. Ex. 2 | 8.84 | × note 1 | — | — | note 3 | | | |
| Com. Ex. 3 | 6.19 | Δ | — | — | note 2 | | | |
| Com. Ex. 4 | 9.96 | × note 1 | — | — | note 3 | | | |
| Com. Ex. 5 | 7.52 | × note 1 | — | — | note 3 | | | |

Experimental Example 3

An adhesive preparation comprising the adhesive material of the above-mentioned Example 3, which has an adhesive layer containing 5% isosorbide dinitrate (ISDN) was prepared and subjected to an in vitro permeability test using the skin removed from a mouse. As a result, percutaneous absorption of ISDN was confirmed.

This application is based on patent application Nos. 235646/2004 and 215433/2005 filed in Japan, the contents of which are hereby incorporated by reference.

The invention claimed is:

1. An adhesive material comprising a support and an adhesive layer laminated on one surface of the support,
   wherein the adhesive layer has an apparent viscosity at 30° C. of $0.2 \times 10^4$ to $10 \times 10^4$ Pa·s and comprises
   (i) first and second synthetic rubbers,
   (ii) a tackifier, and
   (iii) an organic liquid compatible with the first and second synthetic rubbers and the tackifier,
   wherein the first synthetic rubber is a branched aliphatic hydrocarbon having a Staudinger Index of 170-300 cm$^3$/g, and the second synthetic rubber is a branched aliphatic hydrocarbon having a Staudinger Index of 30-60 cm$^3$/g,
   wherein the first synthetic rubber, the second synthetic rubber, and the tackifier are present in a ratio of 10:12-20:2-6 or 10:12-20:7-11 by weight,
   wherein the proportion of the second synthetic rubber relative to the whole weight of the adhesive layer is 30-80%, and
   wherein the organic liquid is selected from higher alcohols, oils and fats, organic solvents, plasticizers, liquid surfactants, hydrocarbons, ethoxylated stearyl alcohol, glycerine fatty acid ester fatty acid ester N-methylpyrrolidone, oleic acid, 1,1-butanediol, and combinations thereof.

2. The adhesive material of claim 1, wherein the organic liquid is contained in a proportion of not more than 20% of the total weight of said adhesive layer.

3. The adhesive material of claim 1 wherein the branched aliphatic hydrocarbon is a 2-methylpropene polymer.

4. The adhesive material of claim 1, wherein the tackifier is an ethylethylene polymer, a 1,2-dimethylethylene polymer or an ethylethylene-1,2-dimethylethylene copolymer having a kinematic viscosity at 40° C. of 200-4000 mm$^2$/s.

5. The adhesive material of claim 1, wherein the tackifier is an alicyclic saturated hydrocarbon resin having a softening point of 70-125° C.

6. The adhesive material of claim 1, wherein the organic liquid is at least one member selected from isopropyl myristate and a branched long-chain alcohol.

7. The adhesive material of claim 6, wherein the branched long-chain alcohol is at least one member selected from isostearyl alcohol and octyldodecanol.

8. The adhesive material of claim 6, wherein the organic liquid is isopropyl myristate, the organic liquid optionally further comprises a branched long-chain alcohol, and a mixing ratio of isopropyl myristate:branched long-chain alcohol is 1:0-4 by weight.

9. An adhesive preparation comprising a percutaneously absorbable drug in the adhesive layer of the adhesive material of claim 1.

10. The adhesive material of claim 1, wherein the first synthetic rubber, the second synthetic rubber, and the tackifier are present in a ratio of 10:12-20:2-6 by weight, and the adhesive material can be easily peeled off from a skin surface after an adhesion period of 2 days.

11. The adhesive material of claim 1, wherein the first synthetic rubber, the second synthetic rubber, and the tackifier are present in a ratio of 10:12-20:7-11 by weight, and the adhesive material can be easily peeled off from a skin surface after an adhesion period of 3 days.

* * * * *

UNITED STATES PATENT AND TRADEMARK OFFICE
CERTIFICATE OF CORRECTION

PATENT NO. : 8,394,404 B2
APPLICATION NO. : 11/196936
DATED : March 12, 2013
INVENTOR(S) : Akemi et al.

It is certified that error appears in the above-identified patent and that said Letters Patent is hereby corrected as shown below:

IN THE CLAIMS:

Claim 1 at column 15, lines 29-30,

"glycerine fatty acid ester fatty acid ester N-methylpyrrolidone" should read

"glycerine fatty acid ester, fatty acid ester, N-methylpyrrolidone"

Signed and Sealed this
Twenty-fourth Day of September, 2013

Teresa Stanek Rea
*Deputy Director of the United States Patent and Trademark Office*